United States Patent
Pernodet et al.

(10) Patent No.: US 9,814,665 B2
(45) Date of Patent: Nov. 14, 2017

(54) METHOD AND COMPOSITIONS FOR IMPROVING SELECTIVE CATABOLYSIS AND VIABILITY IN CELLS OF KERATIN SURFACES

(71) Applicant: ELC Management LLC, Melville, NY (US)

(72) Inventors: Nadine A. Pernodet, Huntington Station, NY (US); Donald F. Collins, Plainview, NY (US); Dawn Layman, Ridge, NY (US); Daniel B. Yarosh, Merrick, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 14/753,748

(22) Filed: Jun. 29, 2015

(65) Prior Publication Data

US 2015/0313830 A1   Nov. 5, 2015

Related U.S. Application Data

(62) Division of application No. 14/142,212, filed on Dec. 27, 2013.

(60) Provisional application No. 61/749,633, filed on Jan. 7, 2013.

(51) Int. Cl.

| A61K 8/66 | (2006.01) |
|---|---|
| A61K 8/99 | (2017.01) |
| A61Q 19/00 | (2006.01) |
| A61Q 19/08 | (2006.01) |
| A61K 8/64 | (2006.01) |
| A61K 8/97 | (2017.01) |
| A61K 8/73 | (2006.01) |

(52) U.S. Cl.
CPC ............... *A61K 8/66* (2013.01); *A61K 8/645* (2013.01); *A61K 8/733* (2013.01); *A61K 8/97* (2013.01); *A61K 8/99* (2013.01); *A61Q 19/00* (2013.01); *A61Q 19/08* (2013.01); *A61K 2800/10* (2013.01)

(58) Field of Classification Search
None
See application file for complete search history.

(56) References Cited

U.S. PATENT DOCUMENTS

| 3,215,724 A | 11/1965 | Strobel et al. |
|---|---|---|
| 3,439,088 A | 4/1969 | Edman |
| 3,781,417 A | 12/1973 | Welters |
| 3,818,105 A | 6/1974 | Coopersmith et al. |
| 4,677,152 A | 6/1987 | Allen et al. |
| 4,702,844 A | 10/1987 | Flesher et al. |
| 5,077,211 A | 12/1991 | Yarosh |
| 5,190,762 A | 3/1993 | Yarosh |
| 5,272,079 A | 12/1993 | Yarosh |
| 5,296,231 A | 3/1994 | Yarosh |
| 2003/0223982 A1 | 12/2003 | Schlotmann et al. |
| 2009/0047309 A1 | 2/2009 | Maes et al. |
| 2009/0220481 A1 | 9/2009 | Maes et al. |
| 2010/0034800 A1 | 2/2010 | Kung et al. |
| 2011/0243983 A1 | 10/2011 | Paufique |
| 2011/0250251 A1 | 10/2011 | Maes et al. |
| 2011/0269694 A1 | 11/2011 | Dal Farra et al. |
| 2011/0294876 A1 | 12/2011 | Kuper et al. |
| 2012/0164121 A1 | 6/2012 | Paufique |
| 2013/0183358 A1 | 7/2013 | Fernandez Botello et al. |
| 2015/0071895 A1 | 3/2015 | Pernodet et al. |

FOREIGN PATENT DOCUMENTS

| CN | 102641223 A | 8/2012 |
|---|---|---|
| JP | 2008115098 | 5/2008 |
| KR | 10-20120024822 | 3/2012 |
| KR | 20120095296 | 8/2012 |
| WO | WO-2009/023416 | 2/2009 |
| WO | WO-2011/143171 | 11/2011 |
| WO | WO-2012/050745 | 4/2012 |
| WO | WO-2014/043009 | 3/2014 |

OTHER PUBLICATIONS

Database GNPD [Online] MINTEL; Feb. 28, 2011 (Feb. 28, 2011); Anonymous: "Night skin rejuvenating gel-cream"; XP002759380; Database accession No. 1495728.
Database GNPD [Online] MINTEL; Jun. 30, 2011 (Jun. 30, 2011); Anonymous: "Smoothing gel"; XP002759381; Database accession No. 1565100.
Database GNPD [Online] MINTEL; Dec. 31, 2012 (Dec. 31, 2012); Anonymous: "Eye serum infusion"; XP002759379; Database accession No. 1949483.
Database GNPD [Online] MINTEL; Jul. 31, 2011 (Jul. 31, 2011); Anonymous: "Night repair concentrate"; XP002759382; Database accession No. 1590338.
Keisuke Ito et al; Caffeine induces G2/M arrest and apoptosis via a novel p53-dependent pathway in NB4 promyelocytic leukemia cells; Journal of Cellular Physiology; vol. 196. No. 2; Jun. 11, 2003 (Jun. 11, 2003); pp. 276-283. XP055284564.
Rossella Russo et al; Role of D-Limonene in Autophagy Induced by Bergamot Essential Oil in SH-SY5Y Neuroblastoma Cells; PLOS ONE;vo 1, 9. No. 11; Nov. 24, 2014 (Nov. 24, 2014). p. e113682. XP055284861.
Supplemental European Search Report; EP13869925; Completion Date: Jun. 30, 2016; dated Jul. 13, 2016.

(Continued)

*Primary Examiner* — Michelle F Paguio Frising
(74) *Attorney, Agent, or Firm* — Julie Blackburn

(57) ABSTRACT

A method for increasing cellular viability in cells of keratin surfaces after exposure to UV light and/or detoxifying cells of debris that impedes healthy metabolic function by topically applying to the keratin surface a composition containing at least one autophagy activator and at least one DNA repair enzyme and a method for making a topical composition comprising the steps of (a) identifying an ingredient that activates cellular autophagy in keratinocyte cultures in vitro, and (b) formulating the ingredient into a topical composition in combination with at least one DNA repair enzyme.

8 Claims, No Drawings

(56) References Cited

OTHER PUBLICATIONS

PCT International Search Report: International Application No. PCT/U32013/078057; Completion Date: Apr. 22, 2014; dated Apr. 24, 2014.

PCT Written Opinion of the International Searching Authority; International Application No. PCT/US2013/078057; Completion Date: Apr. 22, 2014; dated Apr. 24, 2014.

Wang, Chien-Yu, et al.; Genomics and proteomics of immune modulatory effects of a butanol fraction of echinacea purpurea in human dendritic cells; BMC Genomics; Oct. 13, 2008; vol. 9; No. 479; pp. 1-30.

METHOD AND COMPOSITIONS FOR IMPROVING SELECTIVE CATABOLYSIS AND VIABILITY IN CELLS OF KERATIN SURFACES

TECHNICAL FIELD

The invention is in the field of compositions for application to skin which enhance selective catabolysis in skin cells.

BACKGROUND OF THE INVENTION

It is well known that stress and environmental aggressors such as UV light, pollution, and cigarette smoke can be very detrimental to skin and accelerate the appearance of aging. Exposure to stress and environmental aggressors often causes damage to cellular DNA, mitochondria, and cellular proteins, lipids, and tissue. Damaged cellular material found within the cell, for example, cytoplasmic or organelle debris can exert a toxic effect on cells by impeding their normal metabolic processes.

Healthy cells have a normal cleansing process that eliminates damaged cellular material and debris. Such detoxification often occurs through a phagocytic process referred to as autophagy, where the cellular debris is engulfed within a vacuole and degraded with cellular enzymes such as lysozymes. Autophagy and the mechanism of autophagy activation in skin cells is described in U.S. Patent Publication No. 2011/0243983 A1, hereby incorporated by reference in its entirety. There is much interest in formulating skin treatment compositions to contain ingredients that stimulate cellular autophagy because the ability of cells to cleanse and detoxify themselves of debris that otherwise impedes healthy metabolic function is improved. The cleansing through autophagy creates new sources of energy for cellular functions because the degradation products release building blocks such as amino acids that can be recycled by the cell. Improved cellular metabolic function in turn means improved cellular health and longevity and greater resistance to undesirable side effects of aging such as lines, wrinkles, mottled skin, hyperpigmentation, laxity and so on.

DNA repair enzymes are known to repair DNA in various ways. Such enzymes are generally categorized according to the type of DNA base mutagenic damage that is repaired.

It has been discovered that the combination of DNA repair enzymes and autophagy activators most unexpectedly will beneficially affect the normal cellular cleansing processes, promote cellular health and longevity, and minimize the deleterious effects of environment, UV light, pollution, and other environmental insults on skin.

Accordingly it is of interest to maximize the cellular health and longevity of cells, particularly skin cells such as keratinocytes or fibroblasts, by treating them with ingredients that stimulate natural cellular repair processes by, for example, eliminating cellular debris and toxins, and in addition, to maximize the effectiveness of such cellular detoxification by ensuring that the maximum number of detoxification mechanisms are operable. It is also of interest to stimulate detoxification processes where the breakdown of the cellular debris and toxins results in amino acids or other biological molecules that can be recycled by the cell.

Thus, there is a need to maximize cellular health and longevity by stimulating selective catabolysis in cells so that cellular debris and toxins are removed and by products of such degradation may be recycled. More preferably, the selective catabolysis is due to enhancing autophagy activity and promoting DNA repair using DNA repair enzymes.

It has been discovered that compositions containing at least one autophagy activator and at least one DNA repair enzyme in selective cellular catabolysis, that is, cleansing cells of toxic waste products by breaking down the waste products into molecules that may be recycled and used by the cell in normal metabolic functions.

SUMMARY OF THE INVENTION

The invention is directed to a composition for treatment of keratin surfaces to stimulate selective catabolysis comprising at least one autophagy activator and at least one DNA repair enzyme.

The invention is further directed to a method for stimulating selective catabolysis in cells of keratin surfaces by applying to such surfaces a composition comprising at least one autophagy activator and at least one DNA repair enzyme.

DETAILED DESCRIPTION

I. Definitions

All percentages mentioned herein are percentages by weight unless otherwise indicated.

All documents mentioned herein are incorporated by reference in their entirety.

"Autophagy" means the process by which cells cleanse themselves of toxins and debris by forming a membrane around the debris, segregating it from the rest of the cell, and adjoining the formed vacuole with cellular lysosomes, which are cellular organelles that contain acid hydrolase enzymes that break down the cellular debris and waste found in the vacuole.

"Autophagy Activator" means an ingredient that stimulates the normal cellular autophagy processes.

"CLOCK gene activator" means an ingredient that activates one or more CLOCK genes present in keratinocytes.

The term "DNA repair enzyme" means an enzyme that is operable to repair DNA base mutagenic damage. Such enzymes are often categorized by the type of DNA damage they repair, for example BER (base excision repair) enzymes, nucleotide excision repair (NER) enzymes; mismatch repair (MMR) enzymes; DNA helicases; DNA polymerases, and so on. For example, mutations such as 8-oxo-7,8-dihydro-2'-deoxyguanosine may be repaired by OGG1 (8-oxoGuanine glycosylase); T-T dimers which may be repaired by (Nucleotide excision repair (NER) Photolyase); 6-4 photoproducts (which may be repaired by NER); and 06-methyl guanine (which may be repaired by 06-alkyl guanine transferase (AGT)).

The term "keratin surfaces" means skin, hair, and nails.

"PER1 gene activator" means an ingredient that activates one or more PER1 genes found in keratinocytes.

"Proteasome" means a protein complex typically located in the nucleus or cytoplasm of cells that is operable to degrade damaged cellular proteins by proteolysis into smaller subunits which may then be further digested into single amino acids. These recycled amino acids may be used by the cell in the synthesis of new proteins.

"Proteasome activator" means an active ingredient that stimulates the activity of proteasomes in cells of keratin surfaces such as keratinocytes, fibroblasts, etc.

"Recycle" means, with respect to the degradation of cellular debris and toxins, that the debris and toxins may be broken down into molecules such as proteins, lipids, amino acids, or other biological materials that are usable by the cell in its normal healthy metabolic processes.

"Repair" means, with respect to skin cells, that the damaged portions of cells, such as DNA, mitochondria, proteins, lipids, or other cellular materials are reduced or eliminated.

"Selective catabolysis" means, with respect to the cells of keratin surfaces, that the cells are able to cleanse themselves of debris, waste, and toxins selectively without compromising healthy cellular constituents, and preferably by one or more of mechanisms such as activating cellular autophagy or activating cellular proteasome processes.

II. Autophagy Activator

The composition of the invention contains at least one ingredient that is operable to activate normal cellular autophagic processes. The autophagy activator is present in amounts ranging from about 0.00001 to 20%, preferably 0.0001-15%, more preferably from about 0.001 to 10%. In general, the cellular autophagy process comprises four general steps. Step 1 is the initiation of vacuole formation; Step 2 the formation of the initial vacuole or autophagosome which sequesters the cytoplasmic material to be degraded. Step 3 is the maturation of the autophagosome into a degradative vacuole. Step 4 is the actual degradation of the sequestered material.

Ingredients with autophagy activation activity can be identified by their ability to either stimulate or inhibit various cellular metabolic pathways. For example, ingredients that stimulate the expression of MAP-LC3, ATG5-12, protein p53, AMPK, or DRAM are suitable autophagy activators. Ingredients that inhibit the expression of mTOR are also suitable autophagy activators.

The gene MAP-LC3 codes for microtubule-associated protein 1 light chain 3, a protein that initiates formation of autophagosomes. ATG5-12 also stimulates formation of autophagosomes. mTOR, also known as mammalian target of rapamycin, is also known as the mechanistic target of rapamycin or FK506 binding protein 12-rapamycin associated protein 1 (FRAP1). FRAP1 is encoded by the FRAP gene. Any ingredient that inhibits the expression of mTOR, involved in autophagosome creation, will have autophagy activating properties. Also suitable as autophagy activators are ingredients that stimulate expression of protein p53, AMPK, and/or DRAM (damage remedy autophagy modulator protein) in keratinocytes. Protein p53, also known as a tumor suppressor protein, is encoded by the p53 gene. AMPK means AMP activated protein kinase and DRAM, damage related autophagy modulator. Both are known to stimulate autophagy activation in keratinocytes.

Thus any ingredient that has the above mentioned effects on the genes may be suitable autophagy activators. During the autophagocytic process cellular debris such as oxidized proteins and peroxidized lipids are degraded. Such cellular debris often affects normal metabolic function. Screening of ingredients to determine efficacy by ability to stimulate or inhibit cellular, preferably keratinocyte, genes and/or proteins mentioned above may be done according to methods as set forth in US Patent Publication No. 2011/0243983 or other methods known in the art.

For example, one general process for identifying ingredients that may be autophagy activators is by first inducing nutritive stress in cultured cells such as keratinocytes. For example, the cells are first cultured in complete culture medium with growth factors, for about 24 hours. The culture medium is then removed and replaced with a non-nutritive culture medium, for example one that does not contain growth factors. The cells are cultured for about 30 minutes to about 25 hours in a state of nutritive stress. Then, the non-nutritive culture medium is removed and replaced with complete culture medium to promote cellular recovery. Thereafter, the cells are evaluated for autophagocytic activity by measuring the expression of one or more of MAP-LC3; ATGS-12; phosphorylated mTOR; phosphorylated p53; DRAM; or phosphorylated AMPK in those cells. Measurement of such expression can take place by immunofluorescence measurements. In addition, the expression can be ascertained by Western Blot analysis of phosphorylated proteins associated with the expressed genes.

Examples of ingredients that are known to exert either the stimulatory or inhibitory effects on the above mentioned genes which, in turn, stimulate autophagy, are yeast extracts including but not limited to those from the genuses such as *Lithothamnium, Melilot, Citrus, Candida, Lens, Urtica, Carambola, Momordica, Yarrowia, Plumbago*, etc. Further specific examples include *Lithothamniumn calcareum, Melilotus officinalis, Citrus limonum, Candida saitoana, Lens culinaria, Urtica dioica, Averrhoa carambola, Momordica charantia, Yarrowia lipolytica, Plumbago zeylanica* and so on.

Also suitable are ingredients such as amiodarone hydrochloride, GF 109203X which is also referred to as (3-(N-[Dimethylamino]propyl-3-indolyl)-4-(3-indolyl)maleimide 3-[1-[3-(Dimethylamino)propyl]1H-indol-3-yl]-4-(1Hindol-3-yl)1H-pyrrole-2,5dione Bisindolylmaleimide I; N-Hexanoyl-D-sphingosine; Niclosamide; Rapamycin from *Streptomyces hygroscopicus*; Rottlerin which is also referred to as (1-[6-[(3-Acetyl-2,4,6-trihydroxy-5-methylphenyl) methyl]-5,7-dihydroxy-2,2-dimethyl-2H-1-benzopyran-8-yl]-3-phenyl-2-propen-1-one, Mallotoxin); STF-62247, also known as 5-Pyridin-4-yl-thiazol-2-yl-m-tolyl-amine; Tamoxifen; Temsirolimus which is also known as 42-[3-Hydroxy-2-methylpropanoate, CCI-779, Rapamycin; ATG1 autophagy related 1 homolog; ATG1, Serine/threonine-protein kinase ULK1, UNC-51-like kinase; or Z36 which is also referred to as ((Z)-5-Fluoro-1-(3'-dimethylamino)propyl-3-[(5'-methoxyindol-3-ylidene)methyl]-indolin-2-one; or 1-[3-(dimethylamino)propyl]-5-fluoro-1,3-dihydro-3-[(5-methoxy-1H-indol-3-yl)methylene]-2H-Indol-2-one); Bufalin, also referred to as 3β,14-Dihydroxy-5β,20(22)-bufadienolide, 5β,20(22)-Bufadienolide-3β,14-diol. Such ingredients may be purchased from Sigma-Aldrich Chemical Company.

III. DNA Repair Enzyme

The composition contains one or more DNA repair enzymes. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-Guanine base damage.

Another type of DNA repair enzyme that may be used is one that is known to be effective in repairing 06-methyl guanine base damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of various species of *micrococcus*), lecithin, and water. Photosomes® comprise a mixture of plankton extract (which is the extract of marine biomass which includes one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *Bifida* lysate or *Bifida* ferment lysate, the latter a lysate from *Bifido* bacteria which contains the metabolic products and cytoplasmic fractions when *Bifido* bacteria are cultured, inactivated and then disintegrated. This material has the INCI name *Bifida* Ferment Lysate.

Other suitable DNA repair enzymes include Endonuclease V, which may be produced by the denV gene of the bacteriophage T4. Also suitable are T4 endonuclease; $O^6$-methylguanine-DNA methyltransferases; photolyases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; topoisomerase; $O^6$ benzyl guanine; DNA glycosylases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as $O^6$-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch exision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as Xeroderma pigmentosum group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog ((REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial lysates, biological materials, and the like. For example, botanical extracts may contain DNA repair enzymes.

The compositions of the invention may contain one or more DNA repair enzymes.

IV. Other Ingredients

A. Proteasome Activator

The composition may contain one more proteasome activators in amounts ranging from about 0.0001 to 65%, preferably from about 0.0005 to 50%, more preferably from about 0.001 to 40%.

Suitable proteasome activators are any compounds, molecules, or active ingredients that stimulate proteasome activity in the cells of keratin surfaces.

Examples of suitable proteasome activators include, but are not limited to, algin, alginates, hydrolyzed algin, molasses extract, *Trametes* extracts, including extracts from *Trametes versicolor*, olea hydroxol.

The composition of the invention may be in the form of an emulsion, aqueous solution or dispersion, gel, or anhydrous composition. If in the form of an emulsion, it may be a water in oil or oil in water emulsion. If in the form of an emulsion, the composition may contain from about 1-99%, preferably from about 5-90%, more preferably from about 10-85% water and from about 1-99%, preferably from about 5-90%, more preferably from about 5-75% of oil. If in the form of an aqueous suspension or dispersion, the composition may generally contain from about 1-99.9%, preferably from about 5-95%, more preferably from about 10-90% water, with the remaining ingredients being the active ingredients or other formula ingredients.

The composition may additionally contain other ingredients including but not limited to those set forth herein.

B. CLOCK, PER1 Gene Activator

The composition of the invention may contain a CLOCK or PER1 cellular gene activator. Suggested ranges are from about 0.000001 to about 40%, preferably from about 0.000005 to 35%, more preferably from about 0.00001 to 25%. Suitable CLOCK or PER1 activators may be present in the form of botanical extracts, polypeptides, peptides, amino acids, and the like.

1. Peptide CLOCK or PER1 Gene Activator

A particularly preferred CLOCK and/or PER1 gene activator comprises a peptide of the formula (I):

$R_1$-(AA)$_n$-$X_1$-S-T-P-$X_2$-(AA)$_p$-$R_2$

Where (AA)$_n$-$X_1$-S-T-P-$X_2$-(AA)$_p$ is (SEQ ID No. 1) and:

$X_1$ represents a threonine, a serine, or is equal to zero, $X_2$ represents an isoleucine, leucine, proline, valine, alanine, glycine, or is equal to zero, AA represents any amino acid or derivative thereof, and n and p are whole numbers between 0 and 4, $R_1$ represents the primary amine function of the N-terminal amino acid, either free or substituted by a protective grouping that may be chosen from either an acetyl group, a benzoyl group, a tosyl group, or a benzyloxycarbonyl group, $R_2$ represents the hydroxyl group of the carboxyl function of the C-terminal amino acid, substituted by a protective grouping that may be chosen from either a $C_1$ to $C_{20}$ alkyl chain or an $NH_2$, NHY, or NYY group with Y representing a $C_1$ to $C_4$ alkyl chain, wherein the sequence of general formula (I) comprises from about 3 to 13 amino acid residues, said sequence of general formula (I) possibly containing substitutions of amino acids $X_1$ and $X_2$ with other chemically equivalent amino acids;

wherein the amino acids are:
Alanine (A)
Arginine (R)
Asparagine (N)
Aspartic Acid (D)
Cysteine (C)
Glutamic Acid (E)
Glutamine (Q)
Glycine (G)
Histidine (H)
Isoleucine (I)
Leucine (L)
Lysine (K)
Methionine (M)
Phenylalanine (F)
Proline (P)
Serine (S)
Threonine (T)
Tryptophan (W)
Tyrosine (Y)
Valine (V)

More preferred are peptides of the above formula as follows:

```
S-T-P-NH2
Ser-Thr-Pro-NH2
```

(SEQ ID No. 2)
```
Y-V-S-T-P-Y-N-NH2
Tyr-Val-Ser-Thr-Pro-Tyr-Asn-NH2
```

(SEQ ID NO. 3)
```
NH2-V-S-T-P-E-NH2
NH2-Val-Ser-Thr-Pro-Glu-NH2
```

(SEQ ID No. 4)
```
NH2-L-H-S-T-P-P-NH2
NH2-Leu-His-Ser-Thr-Pro-Pro-NH2
```

(SEQ ID No. 5)
```
CH3NH-R-H-S-T-P-E-NH2
CH3-NH-Arg-His-Ser-Thr-Pro-Glu-NH2
```

(SEQ ID No. 6)
```
CH3NH-H-S-T-P-E-CH3NH
CH3-NH-His-Ser-Thr-Pro-Glu-CH3-NH
```

More preferred is the S-T-P—$NH_2$ peptide, SEQ ID No. 4, or mixtures thereof.

Most preferred is a peptide manufactured by ISP-Vinscience under the trademark Chronolux® having the INCI name Tripeptide-32 or Chronogen® having the INCI name Tetrapeptide-26, which has an amino acid sequence of:

(SEQ ID No. 7)
```
S-P-L-Q-NH2
Ser-Pro-Leu-Gln-NH2
```

2. Botanical Extracts

Also suitable as the CLOCK or PER1 gene activator is cichoric acid or isomers or derivatives thereof. Cichoric acid may be synthetic or naturally derived. Synthetic cichoric acid may be purchased from a number of commercial manufacturers including Sigma Aldrich. Cichoric acid may also be extracted from botanical sources that are known to contain cichoric acid such as *Echinacea, Cichorium, Taraxacum, Ocimum, Melissa*, or from algae or sea grasses. More specifically, botanical extracts such as *Echinacea purpurea, Cichorium intybus, Taraxacum officinale, Ocimum basilicum*, or *Melissa officinalis*. The term "cichoric acid" when used herein also includes any isomers thereof that are operable to increase PER1 gene expression in skin cells.

A specific example includes a botanical extract from *Echinacea purpurea* sold by Symrise under the brand name Symfinity™ 1298 which is an extract of *Echinacea purpurea* which is standardized during the extraction process to contain about 3% by weight of the total extract composition of cichoric acid. *Echinacea* extracts from different sources will vary in cichoric acid content, and as such will yield variable results in induction of PER1 gene expression. For example, we have observed that another component commonly found in extracts of *Echinacea*, specifically caftaric acid, does not increase PER1 gene expression in skin cells. Moreover, each species of *Echinacea* will differ in content of phenolic and cichoric acids. Ethanolic extract of the roots of *Echinacea purpura* will provide more cichoric acid than ethanolic extracts of *Echineacea angustifolia* or *Echinacea pallida*. The content of active ingredients in any extract is also very dependent on the method of extraction. For example, it is known that in many cases enzymatic browning during the extraction process will reduce the phenolic acid content of the resulting extract.

C. Sunscreens

It may also be desirable to include one or more sunscreens in the compositions of the invention. Such sunscreens include chemical UVA or UVB sunscreens or physical sunscreens in the particulate form. Inclusion of sunscreens in the compositions containing the whitening active ingredient will provide additional protection to skin during daylight hours and promote the effectiveness of the whitening active ingredient on the skin. If present, the sunscreens may range from about 0.1 to 50%, preferably from about 0.5 to 40%, more preferably from about 1 to 35%.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds of the formula:

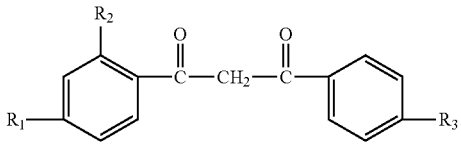

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercially available from Givaudan-Roure under the trademark Parsol® 1789, and Merck & Co. under the tradename Eusolex® 9020.

Other types of UVA sunscreens include dicamphor sulfonic acid derivatives, such as ecamsule, a sunscreen sold under the trade name Mexoryl®, which is terephthalylidene dicamphor sulfonic acid, having the formula:

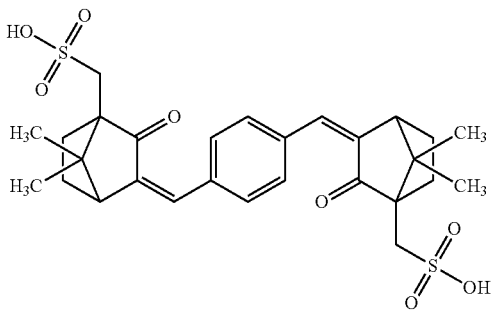 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 10% by weight of the total composition of octocrylene. Suitable amounts range from about 0.001-10% by weight. Octocrylene may be purchased from BASF under the tradename Uvinul® N-539.

Other suitable sunscreens include benzylidene camphor derivatives as set forth in U.S. Pat. No. 3,781,417, which is hereby incorporated by reference in its entirety. Such benzylidene camphor derivatives have the general formula:

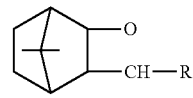

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

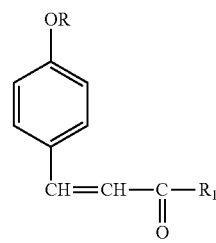

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol® MCX, or BASF under the tradename Uvinul® MC 80.

Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

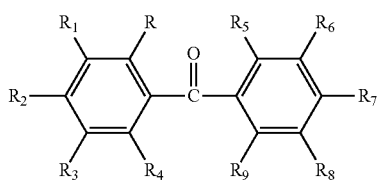

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

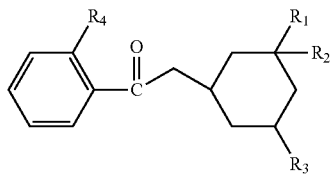

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the trademark Eusolex® HMS and menthyl anthranilate is commercially available from Haarmann & Reimer under the trademark Heliopan®. If present, the Homosalate should be found at no more than about 15% by weight of the total composition.

Various amino benzoic acid derivatives are suitable UVB absorbers including those having the general formula:

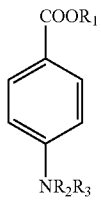

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate 0), ethyldihydroxypropyl PABA, and the like. If present Padimate 0 should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have certain SPF (sun protective factor) values ranging from about 1-50, preferably about 2-45, most preferably about 5-30. Calculation of SPF values is well known in the art.

D. Surfactants

It may be desirable for the composition to contain one more surfactants, especially if in the emulsion form. However, such surfactants may be used if the compositions are solutions, suspensions, or anhydrous also, and will assist in dispersing ingredients that have polarity, for example pigments. Such surfactants may be silicone or organic based. The surfactants will also aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

1. Organic Nonionic Surfactants

The composition may comprise one or more nonionic organic surfactants. Suitable nonionic surfactants include alkoxylated alcohols or ethers, formed by the reaction of an alcohol with an alkylene oxide, usually ethylene or propylene oxide. Suitable alcohols include mono-, di-, or polyhydric short chain (C1-6) alcohols; aromatic or aliphatic saturated or unsaturated fatty (C12-40) alcohols, of cholesterol; and so on.

In one embodiment the alcohol is cholesterol, or an aromatic or aliphatic saturated or unsaturated fatty alcohol which may have from 6 to 40, preferably from about 10 to 30, more preferably from about 12 to 22 carbon atoms. Examples include oleyl alcohol, cetearyl alcohol, cetyl alcohol, stearyl alcohol, isostearyl alcohol, behenyl alcohol, and the like. Examples of such ingredients include Oleth 2-100; Steareth 2-100; Beheneth 5-30; Ceteareth 2-100; Ceteth 2-100; Choleth 2-100 wherein the number range means the number of repeating ethylene oxide units, e.g. Ceteth 2-100 means Ceteth where the number of repeating ethylene oxide units ranges from 2 to 100. Derivatives of alkoxylated alcohols are also suitable, such as phosphoric acid esters thereof.

Some preferred organic nonionic surfactants include Oleth-3, Oleth-5, Oleth-3 phosphate, Choleth-24; Ceteth-24; and so on.

Also suitable are alkoxylated alcohols formed with mono-, di-, or polyhydric short chain alcohols, for example those having from about 1 to 6 carbon atoms. Examples include glucose, glycerin, or alkylated derivatives thereof. Examples include glycereth 2-100; gluceth 2-100; methyl gluceth 2-100 and so on. More preferred are methyl gluceth-20; glycereth-26 and the like.

Other types of alkoxylated alcohols are suitable surfactants, including ethylene oxide polymers having varying numbers of repeating EO groups, generally referred to as PEG 12 to 200. More preferred are PEG-75, which is may be purchased from Dow Chemical under the trade name Carbowax PEG-3350.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

2. Silicone or Silane Surfactants

Also suitable are various types of silicone or silane-based surfactants. Examples include organosiloxanes substituted with ethylene oxide or propylene oxide groups such as PEG dimethicones which are dimethicones substituted with polyethylene glycols including those having the INCI names PEG-1 dimethicone; PEG-4 dimethicone; PEG-8 dimethicone; PEG-12 dimethicone; PEG-20 dimethicone; and so on.

Also suitable are silanes substituted with ethoxy groups or propoxy groups or both, such as various types of PEG methyl ether silanes such as bis-PEG-18 methyl ether dimethyl silane; and so on.

Further examples of silicone based surfactants include those having the generic names dimethicone copolyol; cetyl dimethicone copolyol; and so on.

F. Botanical Extracts

It may be desirable to incorporate one more additional botanical extracts into the composition. If present suggested ranges are from about 0.0001 to 20%, preferably from about 0.0005 to 15%, more preferably from about 0.001 to 10%. Suitable botanical extracts include extracts from plants (herbs, roots, flowers, fruits, seeds) such as flowers, fruits, vegetables, and so on, including yeast ferment extract, *Padina Pavonica* extract, *Thermus Thermophilis* ferment extract, *Camelina Sativa* seed oil, *Boswellia Serrata* extract, olive extract, *Acacia Dealbata* extract, *Acer Saccharinum* (sugar maple), *Acidopholus, Acorus, Aesculus, Agaricus, Agave, Agrimonia,* algae, *aloe, citrus, Brassica,* cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum, Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus, Hordeum Vulgare, Cucumis Sativus, Evernia Prunastri, Evernia Furfuracea, Kola Acuminata,* and mixtures thereof. If desired such botanical extracts may be fermented to increase potency or activity. Fermentation may be accomplished by standard fermentation techniques using bacteria or yeast.

G. Biological Materials

Also suitable are various types of biological materials such as those derived from cells, fermented materials, and so on. If present such materials may range from about 0.001 to 30%, preferably from about 0.005 to 25%, more preferably from about 0.01 to 20%. Examples include fragments of cellular RNA or DNA, probiotic microorganisms, or ferments of microorganisms and organic materials from plants such as leaves, seeds, extracts, flowers, etc. Particularly preferred are RNA fragments.

H. Aqueous Phase Structuring Agent

In the case where the compositions are in the form of aqueous solutions, dispersions or emulsions, in addition to water the aqueous phase may contain one or more aqueous phase structuring agents, that is, an agent that increases the viscosity or, or thickens, the aqueous phase of the composition. This is particularly desirable when the composition is in the form of a serum or gel. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below.

1. Polysaccharides

Polysaccharides may be suitable aqueous phase thickening agents. Examples of such polysaccharides include naturally derived materials such as agar, agarose, alicaligenes polysaccharides, algin, alginic acid, *acacia* gum, amylopectin, chitin, dextran, *cassia* gum, cellulose gum, gelatin, gellan gum, hyaluronic acid, hydroxyethyl cellulose, methyl cellulose, ethyl cellulose, pectin, *sclerotium* gum, xanthan gum, pectin, trehelose, gelatin, and so on.

2. Acrylate Polymers

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymers of A, B, and C monomers wherein A and B are as defined above, and C has the general formula:

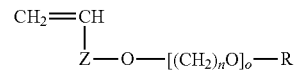

wherein Z is $—(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

$$CH_2=CR'CH_2OB_nR$$

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

Also suitable are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

3. Alkylene Glycols

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

I. Humectants

The composition may contain one or more humectants. If present, they may range from about 0.01 to 75%, preferably from about 0.5 to 70%, more preferably from about 0.5 to 40%. Examples of suitable humectants include glycols, sugars, and the like. Suitable glycols are in monomeric or polymeric form and include polyethylene and polypropylene glycols such as PEG 4-10, which are polyethylene glycols having from 4 to 10 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

J. Oils

In the event the compositions of the invention are in emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C. If present, such oils may range from about 0.01 to 85%, preferably from about 0.05 to 80%, more preferably from about 0.1 to 50%.

1. Volatile Oils

Suitable volatile oils generally have a viscosity ranging from about 0.5 to 5 centistokes 25° C. and include linear silicones, cyclic silicones, paraffinic hydrocarbons, or mixtures thereof.

(a). Volatile Silicones

Cyclic silicones are one type of volatile silicone that may be used in the composition. Such silicones have the general formula:

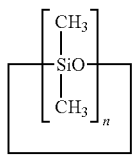

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethyl-pentasiloxane (2 cst) and mixtures thereof, with all viscosity measurements being at 25° C.

Suitable branched volatile silicones include alkyl trimethicones such as methyl trimethicone having the general formula:

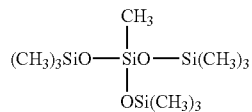

Methyl trimethicone may be purchased from Shin-Etsu Silicones under the tradename TMF-1.5, having a viscosity of 1.5 centistokes at 25° C.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

(a). Esters

Suitable esters are mono-, di-, and triesters. The composition may comprise one or more esters selected from the group, or mixtures thereof (i). Monoesters Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

(b). Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used.

Examples of such oils include castor oil, lanolin oil, $C_{10-18}$ triglycerides, caprylic/capric/triglycerides, sweet almond oil, apricot kernel oil, sesame oil, *camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisoteate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(d). Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

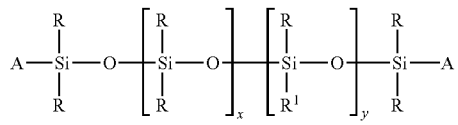

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

K. Vitamins and Antioxidants

It may be desirable to incorporate one or more vitamins or antioxidants in the compositions. If present, suggested ranges are from about 0.001 to 20%, preferably from about 0.005 to 15%, more preferably from about 0.010 to 10%. Preferably such vitamins, vitamin derivatives and/or antioxidants are operable to scavenge free radicals in the form of singlet oxygen. Such vitamins may include tocopherol or its derivatives such as tocopherol acetate, tocopherol ferulate; ascorbic acid or its derivatives such as ascorbyl palmitate, magnesium ascorbyl phosphate; Vitamin A or its derivatives such as retinyl palmitate; or vitamins D, K, B, or derivatives thereof.

L. Preferred Compositions

Preferred compositions are in the aqueous solution or emulsion form and contain at least one autophagy activator and at least one DNA repair enzyme. The composition may optionally contain at least one CLOCK or PER1 gene activator and/or at least one proteasome activator.

More preferred is where within the composition the autophagy activator is a yeast extract that may be fermented and the DNA repair enzyme is one or more of *Arabidopsis thaliana* or ferment thereof. If present the proteasome activator is algin, hydrolyzed algin, or alginate. If present, the nonionic organic surfactant is an alkoxylated alcohol, the chemical sunscreen is a UVB sunscreen, the CLOCK or PER1 keratinocyte gene activator is Tripeptide-32 or Tetrapeptide-26, the DNA repair enzyme, if present, is a mixture of *Arabidopsis Thaliana* extract, *Micrococcus* lysate, *Bifida* Ferment lysate, *Lactobacillus* ferment, and Plankton extract, and the at least one oil is an organic ester or hydrocarbon.

The Method

The invention is also directed to a method for improving normal cellular detoxification processes by treating the cells with a composition that stimulates selective catabolysis by activating or enhancing cellular autophagy processes and/or repairing cellular DNA. In the case where a CLOCK or PER1 gene activator may be present, it may improve the synchronicity of the metabolic pathways of the treated cells, which in turn will improve the efficiency of the autophagy and/or proteasome activation processes.

In the method of the invention, the composition may be applied to keratin surfaces such as skin, scalp, nails or hair one or more times per day. For example, the composition may be applied to skin in the morning prior to beginning daily activities and/or at night prior to retiring. The composition may be applied as part of a regimen; that is, the skin is cleansed and treated with toner, after which the composition of the invention is applied. The composition may be part of a kit containing a cleanser, toner, and the composition of the invention.

Preferably the composition is applied to the face and/or neck and décolletage prior to retiring to repair or eliminate damaged cellular material and provide general improvement of the skin. Combining the composition of the invention at night prior to retiring maximizes the cellular detoxification processes. In general, treatment of skin with the composition of the invention promotes cellular viability, longevity, and health.

The invention will be further described in connection with the following examples which are set forth for the purposes of illustration only.

Example 1

Normal human dermal fibroblasts were harvested and assayed for cellular viability when untreated, treated with solutions containing 0.0025% of DNA repair enzyme *Arabidopsis thaliana* extract, 1% autophagy activator in the form of yeast extract, and a solution containing a mixture of 0.025% *Arabidopsis thaliana* extract and 1% yeast extract autophagy activator.

The fibroblasts were placed in concentrations of 150,000 cells per plate for the 48 hour test, and 300,000 cells per plate for the 24 hour test on 96 well plates. The cells were incubated at 37° C., 5% $CO_2$, and 95% humidity for 24 hours. The test compositions were prepared as follows:
(a) Autophagy Activator. 1% Yeast Extract: 300 ul of yeast extract was added to 14.7 ml of Media Dulbecco's Modified Eagle Media (DMEM) to create a 2% stock solution. Then 2.5 ml of this stock solution was added to 2.5 ml of DMEM to create 1% by weight solution.
(b) DNA Repair Enzyme. Solution of 0.025% *Arabidopsis thaliana* extract: 15 ul of Roxisomes® was combined with 14.985 ml of DMEM and filtered to create a 0.1% stock solution. Then 2.5 ml of this stock solution was diluted with 2.5 ml of DMEM to create a 0.05% solution. Then 2.5 ml of this 0.05% solution was diluted with 2.5 ml of DMEM to make a 0.025% solution of the extract.
(c) Autophagy Activator+DNA Repair Enzyme. 5 ml of the 2% yeast extract solution was mixed with 5 ml of the 0.05% solution of Roxisomes® to form a solution containing 1% yeast extract and 0.025% Roxisomes®.

Normal human dermal fibroblasts were seeded into a 96 well plate at a concentration of 150,000/well and incubated at 37° C. in 5% $CO_2$ for 24 hours to enable cells to acclimate. The next day each well was treated with 200 ul of mixture with each mixture being applied to 6 wells. The plate was incubated at 37° C. for 72 hours with 5% $CO_2$.

A 10% solution of Alamar Blue in 100 ul of DMEM was prepared. 100 ul of a 10% solution of the Alamar Blue reagent was added to each well. The plate was incubated at 37° C., 5% $CO_2$ for 2 hours. The fluorescence was read on a plate reader.

Cells were then irradiated with 10 $J/cm^2$ radiation UV Radiation Chamber (Dr. Groebel, UV-Electronik, GmbH). The DPBS was aspirated and the treatment compositions applied once again for 24 hours. The next morning the medium was aspirated and 100 µl of 10% Alamar Blue solution was added. The plate was incubated at 37° C. for 1.5 to 2 hours. The fluorescence was measured at 530/590 nanometers using a Spectra Max Gemini reader. The cell viability was calculated and expressed as the percentage of survival of cells treated with hydrogen peroxide.

|  | Control | 1% Yeast Extract | 0.025% Roxisomes | 1% Yeast Extract + 0.025% Roxisomes |
|---|---|---|---|---|
| Average Value | 2167.787 | 2564.93 | 1798.29 | 4393.74 |
| Std Dev. | 358.51 | 219.54 | 194.95 | 308.16 |
| Pvalue | 1 | 0.0008012 | 0.001132 | 4.60509E08 |
| % change | 0 | 18.32 | −17.0449 | 102.68 |

*expressed as a percentage increase (or decrease, if a negative number) of the untreated control cells.

The above results demonstrate that when cells are treated with the combination of the autophagy activator and DNA repair enzyme cellular viability is increased 102.68%. Thus, the combination of the autophagy and DNA repair enzyme dramatically improved cellular health and viability both before and after irradiation with UV light.

Example 2

A skin treatment composition in accordance with the invention was prepared as follows:

| Ingredient | w/w % |
|---|---|
| Oleth-3 phosphate | 0.45 |
| Oleth-3 | 0.35 |
| Oleth-5 | 0.24 |
| Butylene glycol | 0.20 |
| Squalane | 0.50 |
| BHT | 0.10 |
| Ethylhexyl methoxycinnamate | 0.10 |
| Choleth-24/ceteth-24 | 0.10 |
| Triethanolamine | 0.11 |
| Retinyl palmitate/*zea mays* (corn) oil/BHT/BHA | 0.10 |
| Butylene glycol | 1.1 |
| Chamomile | 0.03 |
| Bisabolol | 0.10 |
| Water | QS |
| Methyl paraben | 0.46 |
| PEG-75 | 4.00 |
| Bis-PEG-18 methyl ether dimethyl silane | 2.00 |
| Glycereth-26 | 1.00 |
| Methyl gluceth-20 | 4.00 |
| Trisodium EDTA | 0.10 |
| Pantethine | 0.14 |
| Caffeine | 0.05 |
| Xanthan gum | 0.075 |
| Carbomer | 0.26 |
| Triethanolamine | 0.50 |
| Phenoxyethanol | 0.70 |
| Benzyl alcohol | 0.10 |
| Bifida ferment lysate | 9.40 |
| Water/bifida ferment lysate/hydrogenated lecithin | 3.00 |
| Butylene glycol/water/*Cola Acuminata* extract | 3.00 |
| Sodium ribonucleic acid | 0.01 |
| Water/butylene glycol/tripeptide-32* | 0.20 |
| *Lactobacillus* ferment/lecithin/water | 0.05 |
| Water/*Arabidopsis Thaliana* extract/lecithin**** | 0.05 |
| Phenoxyethanol | 0.02 |
| Sodium hyaluronate | 0.01 |
| FD&C Red No. 4 (1% aqueous solution with butylene glycol) | 0.04 |
| FD&C Yellow No. 5 (1% aqueous solution with butylene glycol) | 0.09 |

-continued

| Ingredient | w/w % |
|---|---|
| D&C Green No. 5 (0.1% solution with butylene glycol) | 0.001 |
| Yeast extract** | 0.001 |
| Hydrolyzed Algin (Phyko A1, Codif Recherche & Nature) | 0.001 |
| Water | QS100 |

*CLOCK or PER1 gene activator
**autophagy activator
***proteasome activator
****DNA repair enzyme The composition was prepared by combining the ingredients and mixing well to form a liquid. The composition was stored in brown glass bottles.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for making a topical composition comprising the steps of:
   (a) identifying an extract from the *Candida* genus that activates cellular autophagy in skin cell cultures in vitro by:
      (i) measuring gene expression of mTOR in the cultured skin cells;
      (ii) selecting the extract that shows an inhibition in mTOR gene expression in the cultured skin cells;
   (b) identifying at least one DNA repair enzyme;
   (c) combining the extract of (a) and the DNA repair enzyme of (b) and testing on skin cells in vitro by measuring survival after exposure to UV light at 10 J/cm$^2$;
   (d) selecting the combination of (c) in amounts that provide a synergistic increase in cellular health and viability when tested on skin cells in vitro; and
   (e) adding the selected combination of (d) into a topical composition, wherein the at least one DNA repair enzyme is a base excision repair (BER) enzyme.

2. The method of claim 1 wherein the skin cells are keratinocytes.

3. The method of claim 1 wherein the gene expression measurement is measured by immunofluorescence.

4. The method of claim 1 wherein the gene expression is measured by western blot analysis of phosphorylated proteins associated with the expressed gene.

5. The method of claim 1 wherein the topical composition is in the form of an emulsion prepared by emulsifying oil into a water continuous phase.

6. The method of claim 5 wherein the composition further comprises at least one CLOCK or PER1 gene activator, at least one proteasome activator, or mixtures thereof.

7. The method of claim 1, wherein the BER enzyme is 8-oxoguanine DNA glycosylase (OGG1).

8. The method of claim 1 wherein the extract from the *Candida* genus is *Candida saitoana*.

* * * * *

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial Sequence
<220> FEATURE:
<223> OTHER INFORMATION: CLOCK and/or PER1 gene activator
<220> FEATURE:
<221> NAME/KEY: misc_feature
<222> LOCATION: (1)..(4)
<223> OTHER INFORMATION: Xaa can be any naturally occurring amino acid
      or no amino acid
<220> FEATURE:
<221> NAME/KEY: misc_feature
<222> LOCATION: (5)
<223> OTHER INFORMATION: Xaa can be threonine or serine or no amino acid
<220> FEATURE:
<221> NAME/KEY: misc_feature
<222> LOCATION: (9)
<223> OTHER INFORMATION: Xaa can be isoleucine, leucine, proline,
      valine, alanine, glycine or no amino acid
<220> FEATURE:
<221> NAME/KEY: misc_feature
<222> LOCATION: (10)..(13)
<223> OTHER INFORMATION: Xaa can be any naturally occurring amino acid
      or no amino acid

<400> SEQUENCE: 1

Xaa Xaa Xaa Xaa Xaa Ser Thr Pro Xaa Xaa Xaa Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CLOCK and/or PER1 gene activator

<400> SEQUENCE: 2

Tyr Val Ser Thr Pro Tyr Asn
1               5

<210> SEQ ID NO 3
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 3

Val Ser Thr Pro Glu
1               5

<210> SEQ ID NO 4
<211> LENGTH: 6
```

```
<212> TYPE: PRT
<213> ORGANISM: Artificial Sequence
<220> FEATURE:
<223> OTHER INFORMATION: CLOCK and/or PER1 gene activator

<400> SEQUENCE: 4

Leu His Ser Thr Pro Pro
1               5

<210> SEQ ID NO 5
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 5

Arg His Ser Thr Pro Glu
1               5

<210> SEQ ID NO 6
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 6

His Ser Thr Pro Glu
1               5

<210> SEQ ID NO 7
<211> LENGTH: 4
<212> TYPE: PRT
<213> ORGANISM: Artificial Sequence
<220> FEATURE:
<223> OTHER INFORMATION: CLOCK and/or PER1 gene activator

<400> SEQUENCE: 7

Ser Pro Leu Gln
1               5
```